US012186335B2

(12) United States Patent
Bruning et al.

(10) Patent No.: US 12,186,335 B2
(45) Date of Patent: *Jan. 7, 2025

(54) METHODS AND COMPOSITIONS FOR INHIBITING ENVELOPED VIRUSES USING HIGH MOLECULAR WEIGHT HYDROPHOBICALLY MODIFIED ALKALI SWELLABLE EMULSION POLYMERS AND SURFACTANT

(71) Applicant: Johnson & Johnson Consumer Inc., Skillman, NJ (US)

(72) Inventors: Elizabeth Bruning, Skillman, NJ (US); Anthony Robert Geonnotti, III, Skillman, NJ (US); Euen Thomas Ekman-Gunn, Skillman, NJ (US); Russel Walters, Skillman, NJ (US); Alpana Oak, Skillman, NJ (US); Frank C. Sun, Skillman, NJ (US); Kimberly Capone, Skillman, NJ (US); Frank J. Kirchner, Skillman, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 191 days.

This patent is subject to a terminal disclaimer.

(21) Appl. No.: 16/856,861

(22) Filed: Apr. 23, 2020

(65) Prior Publication Data

US 2021/0330701 A1     Oct. 28, 2021

(51) Int. Cl.
*A61K 31/78*     (2006.01)
*A61K 9/00*     (2006.01)
*A61K 31/085*     (2006.01)
*A61P 31/18*     (2006.01)

(52) U.S. Cl.
CPC ............ *A61K 31/78* (2013.01); *A61K 9/0014* (2013.01); *A61K 31/085* (2013.01); *A61P 31/18* (2018.01)

(58) Field of Classification Search
None
See application file for complete search history.

(56) References Cited

U.S. PATENT DOCUMENTS

| | | |
|---|---|---|
| 3,755,560 A | 8/1973 | Dickert et al. |
| 4,384,096 A | 5/1983 | Sonnabend |
| 4,421,769 A | 12/1983 | Dixon et al. |
| 5,874,495 A | 2/1999 | Robinson |
| 7,157,414 B2 | 1/2007 | Librizzi et al. |
| 7,772,421 B2 | 8/2010 | Yang et al. |
| 7,803,403 B2 | 9/2010 | Librizzi et al. |
| 7,892,525 B2 | 2/2011 | Faivre et al. |
| 8,025,902 B2 | 9/2011 | Librizzi et al. |
| 8,211,850 B2 | 7/2012 | Andjelic et al. |
| 8,293,845 B2 | 10/2012 | Tamareselvy et al. |
| 8,329,626 B2 | 12/2012 | Gunn et al. |
| 8,329,627 B2 | 12/2012 | Gunn et al. |
| 8,343,902 B2 | 1/2013 | Walters et al. |
| 8,623,935 B2 | 1/2014 | Hobbs et al. |
| 9,068,148 B2 | 6/2015 | Tamareselvy et al. |
| 9,931,290 B2 | 4/2018 | Tamareselvy et al. |
| 10,435,308 B2 | 10/2019 | Man et al. |
| 10,517,806 B2 | 12/2019 | Emiru et al. |
| 2002/0051797 A1 | 5/2002 | Jezior |
| 2004/0224005 A1 | 11/2004 | Gabbay |
| 2005/0069566 A1 | 3/2005 | Tamarkin et al. |
| 2005/0244365 A1* | 11/2005 | Labib ................. A61P 31/22 424/78.18 |
| 2008/0139656 A1 | 6/2008 | Taylor et al. |
| 2009/0185995 A1 | 7/2009 | Vochecowicz et al. |
| 2010/0008938 A1 | 1/2010 | Diwan et al. |
| 2014/0234249 A1* | 8/2014 | Capone ................. A61L 15/22 424/78.02 |
| 2016/0262999 A1 | 9/2016 | Pedersen et al. |

FOREIGN PATENT DOCUMENTS

| | | |
|---|---|---|
| EP | 226097 B1 | 11/1986 |
| EP | 705852 B1 | 10/1996 |
| GB | 2346891 A | 8/2000 |
| WO | WO2005074947 | 8/2005 |
| WO | WO 2008/014824 A1 | 2/2008 |
| WO | WO 2008/036587 A2 | 3/2008 |
| WO | WO2008036134 | 3/2008 |
| WO | WO2014130432 | 8/2014 |

OTHER PUBLICATIONS

Robertson et al. (Mar. 1995). "Recombination in AIDS viruses." Journal of Molecular Evolution. 40 (3):249-59.
Liu et al., Research and Development on Therapeutic Agents and Vaccines for COVID-19 and Related Human Coronavirus Diseases, ACS Cent. Sci. 2020, 6, 315-331).
Blaising et al., Arbidol as a broad-spectrum antiviral: An update, Antiviral Research, 107 (2014) 84-94.
Kadam et al., Structural basis of influenza virus fusion inhibition by the antiviral drug Arbidol, PNAS Jan. 10, 2017 114 (2) 206-214.
Matsumura, et al.; "Amphipathic DNA Polymers Inhibit Hepatitis C Virus Infection by Blocking Viral Entry," Gastroenterology, Elsevier Inc., vol. 137, No. 2, Aug. 1, 2009, pp. 673-681.
Fisher Kevin; "Final Report on the Safety Assessment of Nonoxynols -2, -4, -8, -9, -10, -12, -14, -15, -30, -40, and -50," Journal of the American College of Toxicology Volume, vol. 2, No. 7; Jan. 1, 1983; pp. 35-60.
Int'l. Search Report; PCT/IB2021/053205; dated Jun. 30, 2021.
Menachery et al., Pathogenic Influenza Viruses and Coronaviruses Utilize Similar and Contrasting Approaches to Control Interferon-Stimulated Gene Responses, American Society of Microbiology, 2014, 5(3): 1-11.

(Continued)

*Primary Examiner* — Bong-Sook Baek
(74) *Attorney, Agent, or Firm* — Darryl C. Little

(57) ABSTRACT

This invention relates to methods and compositions for inhibiting the transmission of enveloped viruses, which entails applying a composition containing a high molecular weight hydrophobically-modified polymer to an infectable or ingestible surface that may contain viruses and wherein said anti-viral composition comprises less than about 9% by weight of surfactant having an HLB greater than about 12.

12 Claims, 3 Drawing Sheets

(56) References Cited

OTHER PUBLICATIONS

Li, Structure, Function and Evolution of Coronavirus Spike Proteins, Annu. Rev. Virul. 2016, 3(1):237-261.
Sagarin, Cosmetics, Science and Technology, 2nd Edition, vol. 1, pp. 32-43 (1972) and the International Cosmetic Ingredient Dictionary and Handbook, eds. Wenninger and McEwen, pp. 1656-1661, 1626, and 1654-55 (The Cosmetic, Toiletry, and Fragrance Assoc., Washington, D.C., 7th Edition, 1997) (hereinafter "ICI Handbook").
Sagarin, Cosmetics, Science and Technology, 2nd Edition, vol. 1, pp. 72-73 (1972) and the ICI Handbook pp. 1693-1697.
McCutcheon's Detergents and Emulsifiers, North American Edition, pp. 317-324 (1986), and the ICI Handbook, pp. 1673-1686.
Mintel Report Record ID No. 1867920; Neutrogena Ultra Gentle Daily Care Face Cleanser; Date Published Sep. 2012.
Mintel Report Record ID No. 5114245; Johnson's baby moisture wash; Date Published Sep. 2017.
Mintel Report Record ID No. 2165545; Johnson's baby Head-to-Toe washcloths; Published Sep. 2013.
NIH Report; Vaccine Company Develops Nasal Antiseptic That Kills Coronavirus in Lab Studies; https://projectreporter.nih.gov/Reporter_Viewsh.cfm?sl=14E8CD0F4B8AC3D17598B8961CAA4A01A2FFCEB861BF; dated Jun. 30, 2020.
Solvay: "Rheomer 33T datasheet", Sep. 1, 2013 (Sep. 1, 2013), pp. 1-2, XP0931 5421 0, Retrieved from the Internet: URL:https://glenncorp.com/wp-content/uploads/2014/04/Rheomer-33T.PDS_.09.01.1 3.pdf.
Vardanyan R.S., Hruby V.J.; Antiviral Drugs; Chapter in Book "Synthesis of Essential Drugs", Dated 2006, pp. 549-557, p. 549.
Sutyagin V.M. et al., "Chemistry and Physics of Polymers: Textbook" [in Russian], Tomsk: TPU Publishing House, 2003, 208 pages; (see p. 142 para. 1-2 from the bottom, p. 132 para. 4-5 from the bottom, p. 140 para. 2 from the bottom, p. 151 para 1 from the bottom, p. 173 para. 2 from the top).
Maskovskij M.D.; [Drugs], $16^{th}$ed., updated, revised and corrected, Moscow: Novaa Volna, Dated 2012, 1216 pages, p.8.
Kondrat'eva T.S., et al.; Technology of Medicinal Forms: Textbook in 2 volumes, vol. 1, Moscow: Medicine, dated 1991, 496 pages, pp. 36, 37, 74, 76.

\* cited by examiner

METHODS AND COMPOSITIONS FOR INHIBITING ENVELOPED VIRUSES USING HIGH MOLECULAR WEIGHT HYDROPHOBICALLY MODIFIED ALKALI SWELLABLE EMULSION POLYMERS AND SURFACTANT

FIELD OF THE INVENTION

The method of this invention relates to the use of high molecular weight hydrophobically modified polymers to inhibit the transmission of viruses known as "enveloped" viruses. It also relates to compositions containing said high molecular weight hydrophobically modified polymers capable of inhibiting transmission of said viruses.

BACKGROUND OF THE INVENTION

Infections due to enveloped viruses cause common diseases such as herpes simplex, HIV/AIDS, hepatitis B, influenza, chicken pox, shingles, small pox, and respiratory infections. While the seriousness of these diseases can range from moderately bothersome to life-threatening, these infections adversely affect the quality of life of its host and the personal, institutional and economic areas of our society. As a result, there have been substantial efforts to develop means to prevent viral infection and its spread. These efforts are complicated by viral diversity, the numerous means by which viruses are transmitted, including: direct contact, exchange of bodily fluids (e.g. saliva, sexual transmission, breast feeding), and aerosol transmission (e.g. coughing, sneezing, etc.) as well as the highly evolved measures by which viruses escape detection and/or eradication by their hosts. There have been numerous successes in the discovery and commercialization of antiviral agents administered to those who have been infected with a virus. However, these treatments often require medical prescriptions, have unwanted side effects, only work on a narrow range of viral types/strains, and/or have limited efficacy. Topically delivered antiviral treatments must also be non-irritating to the treated tissues, or risk increasing the risk of infection.

Therefore, cost effective and gentle agents with potent, broad-spectrum anti-viral activity which are capable of significantly reducing virus transmission would fill an unmet need in the antiviral armamentarium and help prevent the spread of viral infections, especially if mild properties of such agents could permit and encourage widespread, frequent usage due to superior compatibility with skin, eyes and other mucosal membranes.

Viruses have high mutation and replication rates; these properties allow rapid evolution in response to external selective pressures (i.e. drug), often leading to treatment resistance and relapse. The concern of resistance is especially salient when the antiviral compound targets a specific epitope on the virion. Due to high levels of viral genetic diversity, this narrow specificity also usually limits the range of viruses sensitive to the compound. Alternatively, other topical antiviral treatments, such as surfactants, target non-specific viral regions and are broadly effective at neutralizing diverse viruses, however, these are often irritating and toxic to human cells. Treatments that irritate tissues may result in an increased infection rate; damaging cellular membranes increases their permeability to some types of viral particles. Thus, a non-irritating yet highly effective means for eradicating viruses and significantly reducing their transmission potential would be highly desirable.

Most viruses (e.g., HIV and many animal viruses) have viral envelopes as their outer layer at the stage of their life-cycle when they are between host cells. Robertson et al. (March 1995). "Recombination in AIDS viruses." Journal of Molecular Evolution. 40 (3): 249-59. Some enveloped viruses also have a protein layer called a capsid between the envelope and their genome. Id. The envelopes are typically derived from portions of the host cell membranes (phospholipids and proteins), but include some viral glycoproteins. They may help viruses avoid the host immune system. Glycoproteins on the surface of the envelope serve to identify and bind to receptor sites on the host's membrane. The viral envelope then fuses with the host's membrane, allowing the capsid and viral genome to enter and infect the host.

The cell from which the virus itself buds will often die or be weakened and shed more viral particles for an extended period. The lipid bilayer envelope of these viruses is relatively sensitive to desiccation, heat, and detergents; therefore these viruses are easier to sterilize than non-enveloped viruses, have limited survival outside host environments, and typically transfer directly from host to host. Enveloped viruses possess great adaptability and can change in a short time in order to evade the immune system. Enveloped viruses can cause persistent infections.

Classes of enveloped viruses that contain human pathogens include, e.g., DNA viruses such as Herpesvirus, Poxviruses, Hepadnaviruses, Asfarviridae; RNA viruses such as Flavivirus, Alphavirus, Togavirus, Coronavirus, Hepatitis D, Orthomyxovirus, Paramyxovirus, Rhabdovirus, Bunyavirus, Filovirus; and Retroviruses such as HIV.

COVID-19

Coronaviruses (CoVs) are relatively large viruses containing a single-stranded positive-sense RNA genome encapsulated within a membrane envelope. The viral membrane is studded with glycoprotein spikes that give coronaviruses their crownlike appearance. (See FIG. 1, taken from Liu et al., Research and Development on Therapeutic Agents and Vaccines for COVID-19 and Related Human Coronavirus Diseases, ACS Cent. Sci. 2020, 6, 315-331). While coronaviruses infect both humans and animals, certain types of animals such as bats that host the largest variety of coronaviruses appear to be immune to coronavirus-induced illness. There are four classes of coronaviruses designated as alpha, beta, gamma, and delta. The betacoronavirus class includes severe acute respiratory syndrome (SARS) virus (SARS-CoV), Middle East respiratory syndrome (MERS) virus (MERS-CoV), and the COVID-19 causative agent SARS-CoV-2. Similar to SARS-CoV and MERS-CoV, SARS-CoV-2 attacks the lower respiratory system to cause viral pneumonia, but it may also affect the gastrointestinal system, heart, kidney, liver, and central nervous system leading to multiple organ failure. Current information indicates that SARSCoV-2 is more transmissible/contagious than SARS-CoV.

A number of studies have focused on elucidation of virus structure, virus transmission mechanisms/dynamics, as well as identification of antiviral agents and accurate diagnostics for virus detection. These trends reflect immense interest and desire from the scientific community, including both academic and industrial organizations as well as clinicians, to identify new methods to halt the progression of this epidemic disease and to prevent infection and transmission in the future.

COVID-19 is caused by SARS-CoV-2, a new type of coronavirus in the same genus as SARS-CoV and MERS-CoV. Viral proteins responsible for SARS-CoV-2 entry into host cells and replication are structurally similar to those associated with SARS-CoV. Thus, research and development on SARS and MERS may offer insights that would be beneficial to the development of therapeutic and preventive agents for COVID-19.

Arbidol, CAS No. 131707-23-8, which targets S protein/ACE2, is an inhibitor that may disrupt the binding of the viral envelope protein to host cells and prevent entry of the virus to the target cell has entered into clinical trials for treatment of COVID-19. See Liu et al. above and FIG. 2 below, taken from Blaising et al., Arbidol as a broad-spectrum antiviral: An update, Antiviral Research, 107 (2014) 84-94. See also Kadam et al., Structural basis of influenza virus fusion inhibition by the antiviral drug Arbidol, PNAS Jan. 10, 2017 114 (2) 206-214.

The 2003 emergence of the severe acute respiratory disease coronavirus (SARS-CoV) demonstrated that CoVs are capable of causing outbreaks of severe infections in humans. A second severe CoV, Middle East respiratory syndrome coronavirus (MERS-CoV), emerged in 2012 in Saudi Arabia. More recently, COVID-19 identified in Wuhan, China, in December 2019, has proven particularly detrimental.

Given that the polymers of the invention have shown activity against enveloped viruses, it is expected that polymers of the invention may also show activity against COVID-19 by inhibiting entry of the virus in a host cell. See FIG. 3.

RetroVirox, San Diego, CA, has developed cell-based assays that can be used to evaluate experimental treatments against coronaviruses, including SARS-CoV-2. The Company provides testing with SARS-CoV-2 pseudoviruses to evaluate entry inhibitors against the novel coronavirus causative agent of COVID-19. The pseudovirus assay utilizes HIV pseudoviruses coated with the viral spike (S) protein of SARS-CoV-2 (Wuhan isolate). The assay, which recapitulates the mode of entry of the novel coronavirus, it can be used for, e.g., evaluate small-molecule entry inhibitors targeting the S viral protein, the ACE-2 viral receptor, or host proteases and other targets involved in SARS-CoV-2 viral entry.

U.S. Pat. Nos. 7,803,403 and 8,025,902 to Johnson & Johnson Consumer Inc. disclose personal care compositions that contain a low molecular weight, non-cross linked, linear acrylic copolymer and at least one surfactant; and a method of cleansing using said personal care compositions.

U.S. Pat. Nos. 8,343,902 and 8,329,626 to Johnson & Johnson Consumer Inc. disclose a skin cleansing composition that comprises a low molecular weight, non-crosslinked, linear acrylic copolymer and a non-ethoxylated anionic surfactant.

U.S. Pat. No. 8,329,627 to Johnson & Johnson Consumer Inc. discloses a clear skin cleansing composition that comprises a low molecular weight, non-crosslinked, linear acrylic copolymer and a blend of at least two amphoteric surfactants.

U.S. Pat. No. 8,293,845 to Lubrizol Corp. discloses a method for increasing the critical micelle concentration of a surfactant composition comprising including a linear hydrophobically modified (meth)acrylic polymer in said composition.

U.S. Pat. No. 7,892,525 to Lubrizol Advanced Materials, Inc. discloses antiperspirant compositions that comprise a cationic hydrophobically modified polymeric gelling agent and an acidic antiperspirant compound.

U.S. Pat. No. 9,068,148 to Lubrizol Advanced Materials, Inc. discloses an acrylic polymer blend that comprises at least one crosslinked acrylic copolymer and at least one acrylic linear, non-crosslinked polymer; a method for making the acrylic polymer blend; and method for thickening an aqueous composition comprising the acrylic polymer blend.

U.S. Pat. No. 9,931,290 to Lubrizol Advanced Materials, Inc. discloses a surfactant composition that comprises a surfactant and a crosslinked acrylic copolymer; and a personal care cleansing composition comprising the surfactant composition.

U.S. Pat. No. 10,517,806 to Ecolab USA Inc. claims a foaming antimicrobial dermal cleanser that comprises a cationic active ingredient; a cationic compatible surfactant; a foam boosting agent; a foam structure enhancing agent; a skin conditioning agent; and water. The reference claims a method of reducing bacterial, microbial, fungicidal, or viral population on a dermal tissue of a mammal comprising contacting the dermal tissue with the foaming antimicrobial dermal cleanser. The reference also discloses that cationic active ingredients are antimicrobial agents useful in the present invention and that the foam structure enhancing agent can be polyethyleneglycol. The reference discloses the use of *S. aureus* and *Escerichia coli* as test microbial cultures to test microbial efficacy of the formulas therein.

U.S. Pat. No. 10,435,308 to Ecolab USA, Inc. claims a composition for improving oil removal from an oil/aqueous phase solution by foam fractionation that comprises an associative thickener; a surfactant comprising a sorbitan ester; and a viscoelastic surfactant, wherein the viscoelastic surfactant is a betaine, amine oxide, and/or ethoxylated fatty amine. The reference discloses that the composition may be used in, e.g., cleaning agents, cosmetics, pickles, aqueous pigment pastes, automotive finishes, industrial coatings, printing inks, lubricating greases, plaster paints and wall paints, textile coatings, pharmaceutical preparations, crop protection formulations, filler dispersions, adhesives, detergents, wax dispersions, polishes, auxiliaries for tertiary mineral oil production etc.

U.S. Published Application No. 20160262999 to Ecolab USA, Inc. claims an antimicrobial dermal concentrate that comprises a cationic active ingredient; a foam boosting surfactant; a foam boosting copolymer; a foam stabilizing structure; and water. The reference claims that the concentrate can be used to reduce bacterial, microbial, fungicidal or viral population on a dermal tissue of a mammal. The reference discloses that cationic active" is the ingredient that provides antimicrobial activity. The reference discloses that the concentrate may contain a skin conditioner such as polyethylene glycol.

Menachery et al., Pathogenic Influenza Viruses and Coronaviruses Utilize Similar and Contrasting Approaches To Control Interferon-Stimulated Gene Responses, American Society of Microbiology, 2014, 5(3): 1-11, discloses that influenza viruses and coronaviruses exhibit differences in terms of replication, immune stimulation, and overall lethality.

Li, Structure, Function and Evolution of Coronavirus Spike Proteins, Annu. Rev. Virul. 2016, 3(1):237-261, discusses the evolution of two critical functions of coronavirus spike proteins, receptor recognition and membrane fusion, in the context of the corresponding functions from other viruses and host cells.

The cited references are incorporated by reference in their entirety herein.

Neutrogena Corp, Los Angeles, California, markets and sells a Neutrogena® Ultra Gentle Daily Cleanser product that contains the use of potassium acrylates copolymer as a viscosity increasing agent.

Johnson & Johnson Consumer Inc. markets and sells products, including Johnson's Head to Toe Baby Wash; Johnson's Baby Moisture Wash; and Johnson's Baby Wipes that contain the use of potassium acrylates copolymer as a viscosity increasing agent.

Hand sanitizers are generally used to decrease infectious agents on the hands. They are available as liquids, gels, and foams. Alcohol-based versions and non-alcohol based versions are available. Alcohol-based versions typically contain some combination of isopropyl alcohol, ethanol (ethyl alcohol), or n-propanol, with versions containing 60% to 95% alcohol being the most effective. Care should be taken as they are flammable. Alcohol-based hand sanitizer works against a wide variety of microorganisms. Non-alcohol based versions, which typically contain benralkonium chloride or triclosan, are less effective than alcohol-based ones.

In 2020, BlueWillow Biologics, Inc. launched NanoBio Project nasal antiseptic solution containing OTC monograph benzalkonium chloride. The product is applied by thoroughly swabbing the skin inside of each nostril.

SUMMARY OF THE INVENTION

This invention relates to a method of inhibiting entry of enveloped viruses into cells comprising, consisting essentially of and consisting of contacting said viruses with an anti-viral composition comprising at least one high molecular weight hydrophobically modified polymer in an amount effective to inhibit entry of these viruses into cells. Surprisingly, we have found that low concentrations of certain high molecular weight hydrophobically modified polymers known for their gentle properties are able successfully to inhibit entry of enveloped viruses into host cells and thus inhibit transmission of viruses to the hosts.

We believe that these polymers would not encounter or engender some of the historical problems with antiviral treatments, such as drug resistance, narrow breadth of neutralization and host cellular toxicity. The high molecular weight hydrophobically modified polymers useful in the methods and compositions of this invention are broadly active against several viral types and across multiple viral strains. Additionally, these polymers work through a non-specific mechanism of entry inhibition, thereby increasing their chances for inhibitory success and decreasing the likelihood of resistance. Furthermore, as these polymers are exceptionally gentle on mucosal tissues, they have little or no toxicity to human tissues.

Our bodies are challenged by viruses on a daily basis and our immune system, including our skin barrier, is designed to minimize the number of viruses that reach infectable surfaces. The high molecular weight hydrophobically modified polymers useful in the methods and compositions of this invention block the ability of the virus to bind to and/or enter cells, thereby reducing the probability that an infectious virus can reach a target cell and cause a systemic infection. Viral infection is partially the result of a stochastic process—the more viruses that come in contact with infectable cells, the more likely that tissue is to be infected—therefore, use of these polymers to block infectious viruses benefits the immune system, further reduces chances of infection and promotes general good health. The methods and compositions of this invention using high molecular weight hydrophobically modified polymers are surprisingly effective at reducing the number of infectious virions across a broad range of viral types and strains while remaining gentle and non-irritating to human tissues.

The disclosure may best be understood by reference to the following description taken in conjunction with the accompanying figures, which illustrate particular embodiments.

DETAILED DESCRIPTION OF THE PREFERRED EMBODIMENTS

Figure 1:
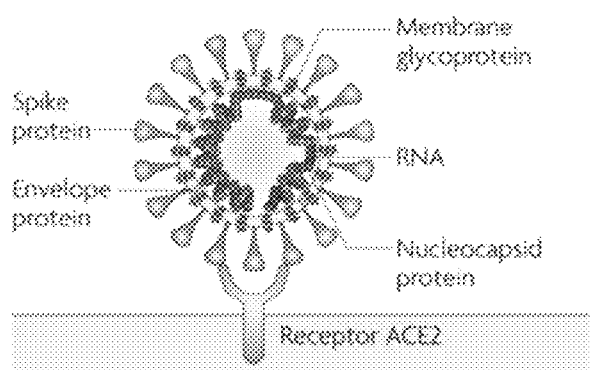
FIG. 1 is an illustration of the coronavirus structure and viral receptor ACE2 on the host cell surface.
Figure 2:
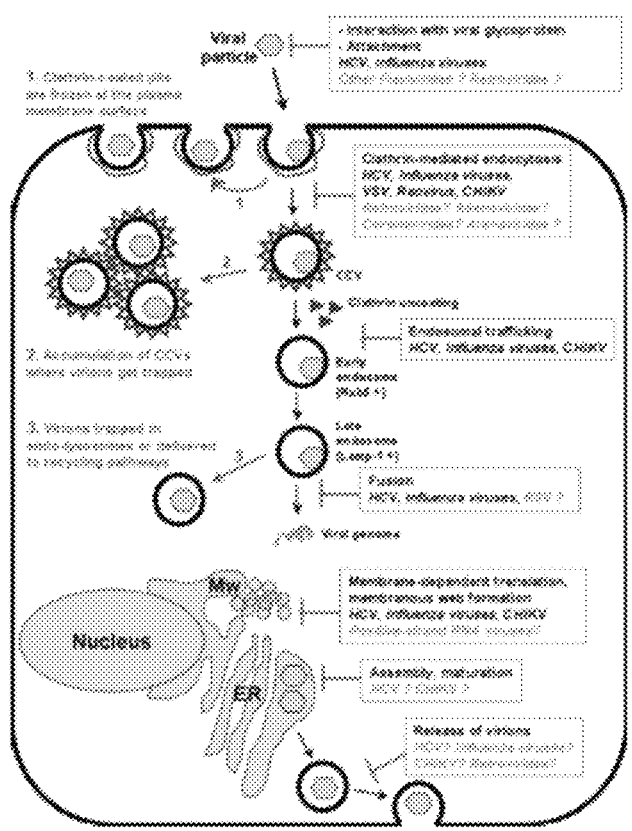
FIG. 2 is an illustration showing broad-spectrum activity of arbidol and its molecular mechanisms of action at the cellular level.
Figure 3:
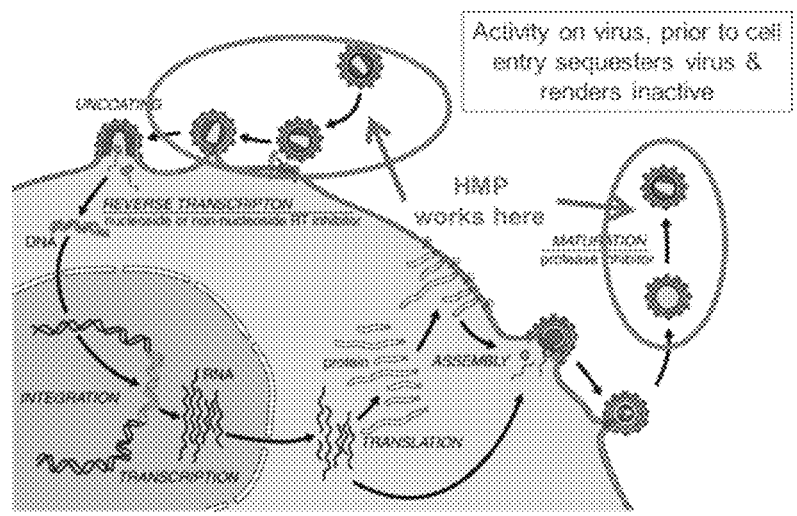
FIG. 3 is an illustration showing the polymers of the invention may show activity against COVID-19 by inhibiting entry of the virus in a host cell.

As used herein, the term "infectable surface" means a surface of a living animal the cells of which may be infected by a virus, including mammals such as human beings. Examples of such infectable surfaces are external skin tissues and mucosal tissues. Mucosal tissues include oral, ocular, nasal, vaginal and rectal tissue.

As used herein, the term "ingestible surface" refers to the surface of foods, including the surface of fruits and vegetables. As used herein, the term "hard surface" refers to surfaces found in the environment such as tables, chairs, walls, and other inanimate surfaces with which skin and/or mucosal tissue may come into contact and on which viruses may reside. The term "internal surface" refers to internal organ surfaces and internal tissues and fluids within the body of a living organism.

As used herein, the term "virus" means a small infectious agent that can replicate only inside the living cells or organisms. Virus particles contain the following parts: genetic material made from either RNA or DNA and a protein coat that protects the genetic material. In some cases, virus particles are surrounded by an envelope of lipids around the protein coat when the virus particles are outside a cell. Virus particles that contain such an envelope of lipids are referred to herein as "enveloped viruses". Enveloped viruses include the following organisms: poxviridae including, but not limited to, molloscum contagiosum, chickenpox, smallpox and other pox viruses, Herpesviridae including herpes simplex virus 1 and herpes simplex virus 2, retroviridae including Lentivirus including Human Immunodeficiency Virus.

As used herein, the term "surfactant" is a surface active agent, or a substance that, when dissolved in water or an aqueous solution, reduces its surface tension or the interfacial tension between it and another liquid.

As used herein, the term "inhibiting transmission" means one or more of the following: (i) impeding the entry of a virus into a host cell; (ii) substantially stopping the introduction of a virus from one individual, infectable surface or contact surface to another; and/or (iii) reducing damage to mucosal membranes such that the membranes retain their integrity and protect against infection by the virus.

As used herein, the hydrophilic-lipophilic balance ("HLB") is a measure of the degree to which a surfactant is hydrophilic or lipophilic, as determined by calculating values for different regions of the surfactant molecule in accordance with methods known to those of skill in the art.

Preferably, the method of this invention relates to a method of inhibiting entry of enveloped viruses into cells comprising, consisting essentially of and consisting of contacting said viruses with an anti-viral composition comprising, consisting essentially of and consisting of at least one high molecular weight hydrophobically modified polymer in an amount effective to inhibit entry of viruses into cells. The methods of this invention further include the application of the compositions set forth herein onto infectable surfaces as well as onto ingestible surfaces. The methods further include contacting viruses with the anti-viral compositions of this invention.

The methods of this invention also include the application of the compositions of this invention to ingestible surfaces such as food as well as to hard surfaces into which skin and mucosal tissue might come into contact. As such, the presence of the compositions of this invention would work to inhibit entry of viruses present on ingestible and hard surfaces into cells contained on skin and mucosa and internal tissues and fluids.

Preferably, the compositions of this invention contain at least about 55% water.

The compositions of this invention may contain surfactant having a Hydrophilic-Lipophilic Balance (hereinafter, "HLB") greater than about 12. Preferably, the compositions of the present invention contain less than about 9% by weight of surfactant having an HLB of greater than about 12. More preferably, the compositions of this invention should contain between about 0.375% and about 9% by weight of surfactant and, most preferably, between about 0.375% and about 6%, even more preferably, between about 0.375% and about 3% by weight of surfactant having an HLB of greater than about 12. Further, the HLB is preferably greater than about 16.

Notwithstanding the foregoing, the compositions of this invention may additionally contain surfactants having an HLB of less than 16. The surfactant levels of the compositions of this invention should be sufficiently low so as not to produce irritation of the skin of a mammal upon exposure or tissue disruption to the cells of the skin or mucosa of said mammal. Such tissue disruption results in providing easier viral entry into the cells. Nonetheless, compositions capable of being used for cleansing as well as virus inhibition are desirable for application to living organisms, including mammals and preferably, humans.

Preferably, the compositions useful in the methods of this invention have a Trans-Epithelial Permeability (hereinafter, "TEP"), as described below, of at least 3.7.

The compositions of this invention may be applied to infectable surfaces of a living entity including mammals, reptiles, birds, fish, bacteria, and the like. Infectable surfaces of these living entities may include, but are not limited to, skin, mucosal and internal tissues. Mucosal tissue includes, but is not limited to oral tissue, nasal tissue, vaginal tissue, rectal tissue or a combination thereof. Importantly, the compositions and methods of this invention do not disrupt these biological surfaces or cause significant irritation of those surfaces.

Polymeric Material

Examples of polymeric materials useful in the compositions and methods of this invention include high-molecular weight hydrophobically modified polymer as described in U.S. Pat. No. 7,772,421. In particular, the polymer should have the following characteristics:

(a) about 25 to about 70 weight percent based on total monomers of at least one $C_3$-$C_8$ alpha beta-ethylenically unsaturated carboxylic acid monomer of the structure (II):

$$RCH{=}C(R')COOH \quad \text{(II)}$$

wherein R is H, $CH_3$, or —$CH_2COOX$; and wherein if R is H, then R' is H, $C_1$-$C_4$ alkyl, or —$CH_2COOX$; if R is —C(O)OX, then R' is H or —$CH_2C(O)OX$; or if R is $CH_3$, then R' is H; and X, if present, is H or $C_1$-$C_4$ alkyl;

(b) about 30 to about 70 weight percent based on total monomers of at least one copolymerizable non-ionic $C_2$-$C_{12}$ alpha beta-ethylenically unsaturated monomer of the structure (III):

$$H_2C{=}CYZ \quad \text{(III)}$$

wherein Y is H, $CH_3$, or Cl; Z is CN, Cl, —COOR', —$C_6H_4R'$, —COOR", or —$HC{=}CH_2$; and wherein R is $C_1$-$C_8$ alkyl or $C_2$-$C_8$ hydroxy alkyl; and wherein R' is H, Cl, Br, or $C_1$-$C_4$ alkyl; and R" is $C_1$-$C_8$ alkyl; and (c) about 0.05 to about 20 weight percent based on total monomer weight of at least one ethylenically unsaturated monomer represented by the structure selected from a group consisting of structures IV, VI and VII;

wherein structure IV represents an ester of an alkoxylated fatty alcohol (IV)

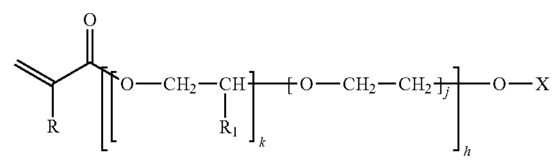

wherein R is H or $CH_3$; wherein $R_1$ is a —$(CH_2)_pH$ alkyl chain; wherein p is an integer from 1 to about 4; wherein j is an integer from 1 to about 50; wherein k is an integer from 0 to about 20; wherein h is 1 or 2; and wherein X has the following structure (V):

(V)

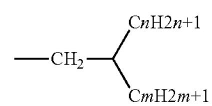

wherein m and n are, independently, are positive integers from 1 to 39 and m+n represents an integer from 4 to 40;

wherein structure VI is an ester of an alkoxylated nopol (VI)

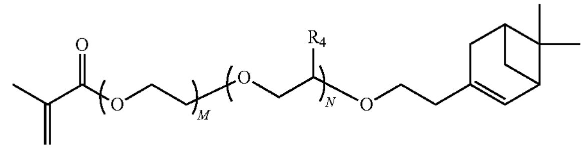

wherein $R_3$ is H or $CH_3$; $R_4$ is an alkyl chain containing 1 to about 4 carbons; M is an integer from 1 to about 50; and N is 0 or an integer of less than or equal to M, and wherein said structure, VII, represents an ester of an alkoxylated fatty alcohol

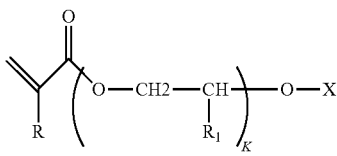

wherein $R_1$ is either H or methyl or ethyl or propyl or combination of any of them, K is an integer from 1 to about

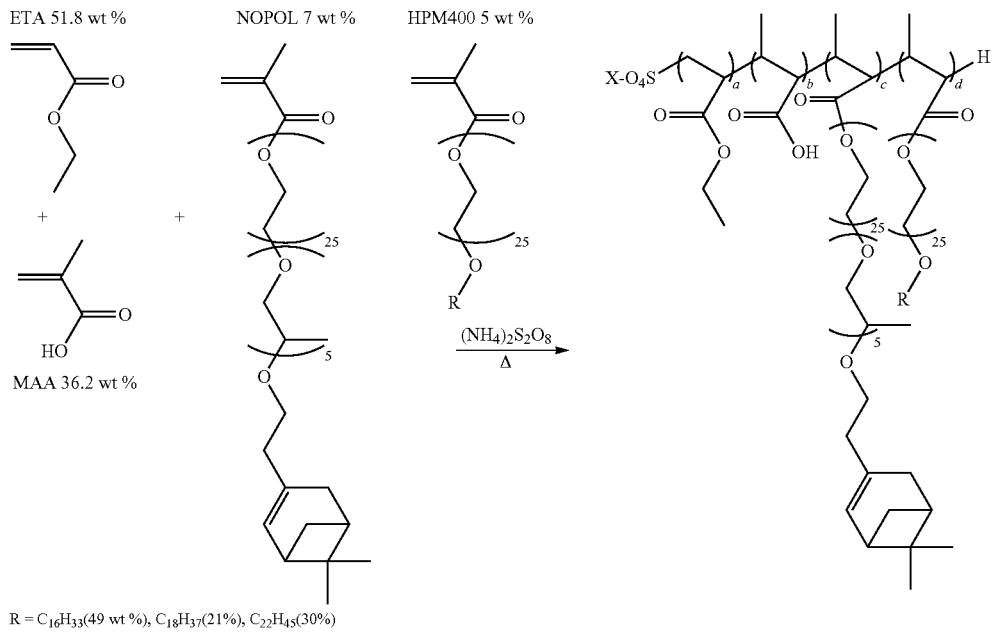

500, R is methyl or ethyl or propyl or butyl and X is H or a moiety represented by structure V.

In a preferred embodiment of the present invention, the high-molecular weight hydrophobically modified polymer is preferably a hydrophobically-modified alkali-swellable emulsion (HASE) polymer such as those described in EP 226097 B1, EP 705852 B1, U.S. Pat. Nos. 4,384,096, and 5,874,495 and 8,211,850 B2, the disclosures of which are incorporated herein by reference. HASE polymers that we believe may be useful in the compositions and methods of this invention include, but are not limited to the following: Acrylates/Steareth-20 Methacrylate Copolymer, Acrylates/Steareth-20 Methacrylate Crosspolymer, Acrylates/Ceteth-20 Itaconate Copolymer), Acrylates/Beheneth-25 Methacrylate Copolymer (available commercially as ACULYN™ 28 from Dow Chemical Company of Midland, MI), hydrophobically modified anionic thickener (available commercially as ACRYSOL™ TT-935 from Dow Chemical Company of Midland, MI), and polyacrylate-33. Most preferably, the HASE polymer used in the compositions and methods of this invention is Polyacrylate-33, sold under the tradename of Rheomer® 33 (available from Rhodia, Cranbury, NJ). Such high-molecular weight hydrophobically modified polymer, when formulated into low-to-medium surfactant-containing cleanser, is shown to display high thickening efficiency and good suspension properties and shear-thinning rheology.

This polymer is formed in an emulsion polymerization with a seed step. The monomers are pre-emulsified in aqueous phase (water and surfactant) and then semi-continuously added to the polymerization reactor. Rheomer® 33 is a copolymer of methacrylic acid (MAA), ethyl acrylate (EtA), Sipomer HPM300 and HPM400 in the following proportions 36.2/51.8/5/7wt % respectively. The finished product is a 30% wt. latex in water. The polymer is formed via the following reaction scheme:

As used herein the term "high molecular weight" polymer refers to a polymer having a number average molecular weight ($M_n$) of at least about 100,000 or more as measured by gel permeation chromatography (GPC) calibrated with a poly(methyl methacrylate) (PMMA) standard. In certain preferred embodiments, high-molecular weight polymers are those having molecular weight ranges of from about 100,000 to about 700,000 $M_n$, more preferably from about 200,000 to about 700,000 $M_n$, and more preferably between about 400,000 and 700,000 $M_n$.

A "hydrophobic moiety" is hereby defined as a nonpolar moiety that contains at least one of the following: (a) a carbon-carbon chain of at least four carbons in which none of the four carbons is a carbonyl carbon or has a hydrophilic moiety bonded directly to it; (b) two or more alkyl siloxy groups ($—[Si(R)_2—O]—$); and/or (c) two or more oxypropylene groups in sequence. A hydrophobic moiety may be, or include, linear, cyclic, aromatic, saturated or unsaturated groups. In certain preferred embodiments, hydrophobic moieties comprise a carbon chain of at least six or more carbons, more preferably seven or more carbons in which none of the carbons in such chain have a hydrophilic moiety bonded directly thereto. Certain other preferred hydrophobic moieties include moieties comprising a carbon chain of about eight or more carbon atoms, more preferably about 10 or more carbon atoms in which none of the carbons in such chain have a hydrophilic moiety bonded directly thereto. Examples of hydrophobic functional moieties may include esters, ketones, amides, carbonates, urethanes, carbamates, or xanthate functionalities, and the like, having incorporated therein or attached thereto a carbon chain of at least four carbons in which none of the four carbons has a hydrophilic moiety bonded directly to it. Other examples of hydrophobic moieties include groups such as poly(oxypropylene), poly (oxybutylene), poly(dimethylsiloxane), fluorinated hydrocarbon groups containing a carbon chain of at least four carbons in which none of the four carbons has a hydrophilic moiety bonded directly to it, and the like.

As used herein, the term "hydrophilic moiety," is any anionic, cationic, zwitterionic, or nonionic group that is polar. Nonlimiting examples include anionics such as sulfate, sulfonate, carboxylic acid/carboxylate, phosphate, phosphonates, and the like; cationics such as: amino, ammonium, including mono-, di-, and trialkylammonium species, pyridinium, imidazolinium, amidinium, poly(ethyleneiminium), and the like; zwitterionics such as ammonioalkylsulfonate, ammonioalkylcarboxylate, amphoacetate, and the like; and nonionics such as hydroxyl, sulfonyl, ethyleneoxy, amido, ureido, amine oxide, and the like.

As used herein, the term "hydrophobically-modified material" refers generally to any material having one or more hydrophobic moieties attached thereto or incorporated therein. Certain preferred hydrophobically-modified materials include materials having a hydrophobe comprising six carbons ($C_6$) or more, preferably eight carbons ($C_8$) or more, more preferably from 10 to 16 carbons ($C_{10-16}$). Examples of certain types of preferred hydrophobically-modified materials include hydrophobically-modified polymers. Such polymers may be formed, for example, by polymerizing one or more hydrophobic monomers and, optionally, one or more co-monomers, to form a polymer having hydrophobic moieties incorporated therein, and/or also by reacting polymer materials with compounds comprising hydrophobic moieties to attach such compounds to the polymers. The high molecular weight hydrophobically modified polymers useful in the compositions and methods of this invention are preferably present in said compositions in amounts that are effective to inhibit substantially the entry of enveloped viruses into cells and/or to inhibit virus transmission to cells. Accordingly, the compositions and methods of this invention inhibit virus entry into said cells and results in the reduction of the potential for viral infection. Preferably, they should be present in the compositions of this invention in an amount of from about 0.00005% to about 3% percent by weight of the composition. More preferably, the high molecular weight hydrophobically modified polymers are present in an amount of from about 0.00005% to about 0.5 percent by weight of the composition. Most preferably, the high molecular weight hydrophobically modified polymers are present in an amount of from about 0.00005% to about 0.01% percent by weight of the composition.

The compositions of this invention may be in the form of a lotion or liquid capable of being applied on the surface of the skin or on an inanimate surface that can contain viruses or bacteria. It may also be a composition which is applied to a mucosal surface such as the surfaces of the nasal cavity or vaginal cavity and can be used as a vaginal microbicide. These types of composition may be more viscous and may be based on a gel formation. The compositions of this invention may be coated onto an absorbent article such as a vaginal or nasal tampon for placement in contact with mucosal surfaces to inhibit viruses in such biologic environments. The compositions of this invention may also be formulated in such a delivery form that they may be injected into the body at appropriate sites where viruses may reside on internal surfaces.

The compositions of this invention may be made into a wide variety of product types that include but are not limited to liquids, lotions, creams, gels, sticks, sprays, shaving creams, ointments, cleansing liquid washes and solid bars, shampoos, pastes, powders, mousses, wipes, patches, wound dressing and adhesive bandages, hydrogels and films. These product types may contain several types of cosmetically acceptable topical carriers including, but not limited to solutions, emulsions (e.g., microemulsions and nanoemulsions), gels, solids and liposomes. The following are nonlimiting examples of such carriers. Other carriers may be formulated by those skilled in the art of formulating such product types.

Preferred compositions of the invention include polymer containing gels; polymer containing drops, including, e.g., eye drops; polymer containing contact lens solutions; polymer containing sprays, e.g., face/body sprays, nasal sprays, and mouth and throat sprays; and polymer containing inhalants.

The compositions of the invention may also be used as a coating on or in personal protective equipment. Personal protective equipment, which is commonly referred to as "PPE", is any equipment worn to minimize exposure to a variety of hazards. Examples of PPE include full body suits, gloves, gowns, masks, respirators and eye and foot protection.

The topical compositions useful in the methods of this invention may be formulated as solutions. Solutions preferably contain an aqueous solvent (e.g., from about 50% to about 99.99% or from about 90% to about 99% of a cosmetically acceptable aqueous solvent).

Topical compositions useful in the methods of this invention may be formulated as a solution containing an emollient. Such compositions preferably contain from about 2% to about 50% of an emollient(s). As used herein, "emollients" refer to materials used for the prevention or relief of dryness, as well as for the protection of the skin. A wide variety of suitable emollients is known and may be used herein. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., $7^{th}$ Edition, 1997) (hereinafter "ICI Handbook") contain numerous examples of materials for use in the compositions and methods of this invention.

A lotion may also be made from such a solution. Lotions preferably contain from about 1% to about 20% (more preferably, from about 5% to about 10%) of an emollient(s) and from about 50% to about 90% (more preferably, from about 60% to about 80%) of water.

Another type of product that may be formulated from a solution is a cream. A cream preferably contains from about 5% to about 50% (more preferably, from about 10% to about 20%) of an emollient(s) and from about 45% to about 85% (more preferably from about 50% to about 75%) of water.

Yet another type of product that may be formulated from a solution is an ointment. An ointment may contain a simple base of animal or vegetable oils or semi-solid hydrocarbons. An ointment may preferably contain from about 2% to about 10% of an emollient(s) plus from about 0.1% to about 2% of a thickening agent(s). A more complete disclosure of thickening agents or viscosity increasing agents useful herein may be found in Sagarin, Cosmetics, Science and Technology, 2nd Edition, Vol. 1, pp. 72-73 (1972) and the ICI Handbook pp. 1693-1697.

The topical compositions useful in the methods of this invention may also be formulated as emulsions. If the carrier is an emulsion, preferably from about 1% to about 10% (e.g., from about 2% to about 5%) of the carrier contains an emulsifier(s). Emulsifiers may be nonionic, anionic or cationic. Suitable emulsifiers are set forth in, for example, U.S. Pat. Nos. 3,755,560, 4,421,769, McCutcheon's Detergents and Emulsifiers, North American Edition, pp. 317-324 (1986), and the ICI Handbook, pp. 1673-1686, which are incorporated herein by reference.

Lotions and creams may also be formulated as emulsions. Preferably such lotions contain from 0.5% to about 5% of an emulsifier(s). Such creams would preferably contain from about 1% to about 20% (more preferably, from about 5% to about 10%) of an emollient(s); from about 20% to about 80% (more preferably, from 30% to about 70%) of water; and from about 1% to about 10% (more preferably, from about 2% to about 5%) of an emulsifier(s).

Other compositions useful in the methods of this invention include gels and liquid compositions that may be applicable to mucosal surfaces for inhibiting viral transmission. Mucosal surfaces include but are not limited to the vagina, rectum, nasal passages, mouth and throat. Preferably, such compositions should include at least one polyhydric alcohol, including glycerin, polyethylene glycol, propylene glycol, sorbitol or a combination thereof. Other polyhydric alcohols know to those of ordinary skill in the art may be used in the compositions and methods of this invention, including polyethylene glycols ranging from molecular weight of from about 300 to about 1450. Preferably, there should be from about 0.1 to about 50% by weight of glycerin and from about 2 to about 40% by weight of propylene glycol.

The mucosal compositions of this invention should also contain one or more water-soluble cellulose-derived polymers. Preferably, such polymers should be a cellulose gum such as one or more hydroxyalkylcellulose polymer. More preferably, the hydroxyalkylcellulose polymer should be one or more of hydroxyethylcellulose, hydroxymethylcellulose, hydroxypropylcellulose, hydroxypropylmethylcellulose and the like. Preferably, the cellulose-derived polymer should be present in the compositions of this invention in the amount of from about 0.1 to about 2% by weight of the composition.

The compositions of this invention intended for vaginal use may also contain one or more spermicides including but not limited to nonoxynol-9 and the like. Although such spermicides may be classified as surfactants, they generally have an HLB of less than 16 and are not useful as or in cleansing compositions and do not foam.

Preferably, an inorganic base may be used to adjust the pH of the composition to be compatible with the vaginal, oral or rectal mucosa. Potassium hydroxide or another alkali metal or alkaline earth metal base may be useful to provide the appropriate pH. Of course, any other physiological acceptable base may also be used in this manner. From about 0.05 to about 5% by weight inorganic base is preferably used.

The compositions of this invention may be prepared in accordance with those methods and processes known to those of skill in the art, or in accordance with the methods of preparation of this invention. For example, water-soluble components such as glycerin, propylene glycol, sorbitol, inorganic base, preservatives, and the like may be dissolved in water and to that combination cellulose-derived polymers may be added. Another method of preparation is mixing all the ingredients into a slurry without water, and then adding the slurry to water.

The composition is preferably substantially free of surfactant, including anionic, cationic, amphoteric, or nonionic surfactants.

Included in a liquid or lotion formation of the composition may be water, oils, preservatives, emulsifiers, viscosity enhancers, emollients, electrolytes, fragrance, buffers, pH modifiers, skin protectants, metal ion sequestrants and the like.

The compositions of this invention may be useful in formulating hand and/or body washes, fruit and/or vegetable washes, ingestible compositions, suppositories, nasal sprays, post-surgical tampons and the like, which may be applied to surfaces or placed in the body to inhibit transmission of viruses. The compositions of this invention may be coated onto an absorbent article such as a vaginal or nasal tampon for placement in contact with mucosal surfaces to inhibit viruses in such biologic environments.

Methods

There are various testing methods that have been employed herein to evaluate different aspects of the methods and compositions of this invention and their effects upon skin, mucosa and viruses when exposed to the compositions of the invention. The Trans-Epithelial Permeability ("TEP") test is used in the instant methods and in the following Examples. The TEP test is used to determine the degree to which a composition causes irritation to the skin or mucosa.

Trans-Epithelial Permeability Test ("TEP Test"):

Irritation to the eyes and/or skin expected for a given formulation is measured in accordance with the Invittox Protocol Number 86 (May 1994), the "Trans-epithelial Permeability (TEP) Assay" and set forth in U.S. Pat. No. 7,157,414, which are incorporated herein by reference. In general, the ocular and/or skin irritation potential of a product may be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that leaks through to the lower well after 30 minutes, as determined spectrophotometrically. The fluorescein leakage is plotted against the concentration of test material to determine the $EC_{50}$ (the concentration of test material that causes 50% of maximum dye leakage, i. e., 50% damage to the permeability barrier). Higher scores are indicative of milder formulas.

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma; causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

Evaluation of Activity Against HIV-1$_{IIIB}$ in CEM-SS Cells

Fifty microliters (50 μL) of CEM-SS cells at a density of 2.5×10$^3$ cells/well in 10% complete Roswell Park Memorial Institute Medium ("RPMI")-1640 (10% FBS with 1% L-glutamine and 1% Penicillin/Streptomycin, available commercially from Invitrogen located in Carlsbad, California) media are plated in a 96-well round bottom plate. One-hundred microliters (100 μL) of each polymer at 6 concentrations are added in triplicate followed by 50 μL of HIV-1$_{IIIB}$ at a pre-determined titer. The cultures are incubated for 6 days at 37° C./5% CO$_2$. Following the incubation, the cells are stained with XTT for evaluation of compound efficacy and cellular toxicity, as described below. AZT is evaluated in parallel as an assay positive control compound.

XTT Staining for Cell Viability and Compound Cytotoxicity:

TC$_{50}$ values for the test materials are derived by measuring the reduction of the tetrazolium dye XTT (2,3-bis(2-methoxy-4-nitro-5-sulfophenyl)-5-[(phenyl amino)carbonyl]-2H-tetrazolium hydroxide). XTT in metabolically active cells is metabolized by the mitochondrial enzyme Nicotinamide adenine dinucleotide phosphate oxidase ("NADPH") to a soluble formazan product. XTT solution is prepared daily as a stock of 1 mg/ml in RPMI-1640 without additives. Phenazine methosulfate (PMS) solution is prepared at 0.15 mg/ml in DPBS and stored in the dark at −20° C. XTT/PMS stock is prepared immediately before use by adding 40 μL of PMS per ml of XTT solution. Fifty μL (50 μL) of XTT/PMS is added to each well of the plate and the plate incubated for 4 hours at 37° C. The 4 hour incubation has been empirically determined to be within the linear response range for XTT dye reduction with the indicated numbers of cells for each assay. The plates are sealed and inverted several times to mix the soluble formazan product and the plate is read at 450 nm (650 nm reference wavelength) with a Molecular Devices SpectraMax Plus 384 96 well plate format spectrophotometer.

Materials:

A high molecular weight hydrophobically modified alkali swellable emulsion (HASE) polymer, Polyacrylate-33 (available as Rheomer® 33 from Rhodia, Cranbury, New Jersey) was used in the compositions of this invention as the high molecular weight hydrophobically modified polymer.

Example 1

Inventive Examples E1-E5 and Comparative Examples C1-C3: Preparation of Compositions to be Tested Inventive examples E1-E5, and Comparative examples C1-C3 were prepared according to the descriptions set forth below with materials in the amounts listed in Table 1.

TABLE 1

Each of the compositions of Table 1 was independently prepared as follows:

| Ingredient | E1 | E2 | E3 | E4 | E5 | C1 | C2 | C3 |
|---|---|---|---|---|---|---|---|---|
| INCI name | w/w % | w/w % | w/w % | w/w % | w/w % | w/w % | w/w % | w/w % |
| Polyacrylate-33 | 0.75 | 3.0 | 0.0375 | 0.18 | 0.09 | | | 9.90 |
| Lauryl Glucoside (unpreserved) | 0.375 | 9.0 | 0.375 | 9.0 | 9.0 | | | |
| Ammonium Laureth Sulfate | | | | | | 14.5 | 14.5 | |
| Cocamide MEA | | | | | | 2.1 | 2.1 | |
| Ammonium Xylene Sulfonate | | | | | | 0.8 | 0.8 | |
| Acrylates/C10-C30 alkyl acrylate cross-polymer | | | | | | | 0.3 | |
| DMDM Hydantoin | | | | | | 0.4 | 0.4 | |
| C1 | | | | | | | | 90.10 |
| Sodium Hydroxide | Qs | qs | qs | | | | | qs |
| Water | Qs | qs | qs | qs | qs | | | |

E1-2.67 gms of Polyacrylate-33 (28% activity) was added to 96.62 gms of deionized water and stirred on a mixing plate, heating to 65° C. until Polyacrylate-33 was completely mixed and uniform. 0.71 gms of Lauryl Glucoside (52.5% activity) was added to the mixture at 40° C. and mixed until uniform. pH was adjusted to 6.55 using 20% sodium hydroxide solution.

E2-10.71 gms of Polyacrylate-33 (28% activity) was added to 71.88 gms of deionized water and stirred on a mixing plate, heating to 65° C. until Polyacrylate-33 was completely mixed and uniform. 17.41 gms of Lauryl Glucoside (52.5% activity) was added to the mixture at 40° C. and mixed until uniform. pH was adjusted to 6.53 using 20% sodium hydroxide solution.

E3 - 0.14 gms of Polyacrylate-33 (28% activity) was added to 99.15 gms of deionized water and stirred on a mixing plate, heating to 65° C. until Polyacrylate -33 was completely mixed and uniform. 0.71 gms of Lauryl Glucoside (52.5% activity) was added to the mixture at 40° C. and mixed until uniform. pH was measured at 6.62

E4-0.64 gms of Polyacrylate-33 (28% activity) was added to 82.22 gms of deionized water and stirred on a mixing plate, heating to 65° until Polyacrylate -33 was completely mixed and uniform. 17.14 gms of Lauryl Glucoside (52.5% activity) was added to the mixture at 40° C. and mixed until uniform. pH was adjusted to 6.53 using 20% citric acid solution.

E5-0.32 gms of Polyacrylate-33 (28% activity) was added to 82.54 gms of deionized water and stirred on a mixing plate, heating to 65° C. until Polyacrylate-33 was completely mixed and uniform. 17.14 gms of Lauryl Glucoside (52.5% activity) was added to the mixture at 40° C. and mixed until uniform. pH was adjusted to 6.50 using 20% citric acid solution.

C1-14.5 gms of Ammonium Laureth Sulfate was added to 82.2 gms of deionized water and heated to 55-60° C. with continuous mixing. 0.8 gms of Ammonium Xylene Sulfonate and 2.1 gms of Cocamide MEA were added to the mixture one after the other with continuous mixing uniform. The mixture was allowed to cool and 0.4 gms of DMDM Hydantoin was added to the mixture at 40° C. pH was adjusted to 6.43 using 20% citric acid solution.

C2-0.3 gms of Acrylates/C10-C30 alkyl acrylate cross-polymer was added to 81.9 gms of deionized water with continuous mixing and heating to 55-60° C. 14.5 gms of Ammonium Laureth Sulfate, 0.8 gms of Ammonium Xylene Sulfonate and 2.1 gms of Cocamide MEA were then added to the mixture, one after the other with continuous mixing until uniform. The mixture was allowed to cool and 0.4 gms of DMDM Hydantoin was added to the mixture at 40° C. pH was adjusted to 6.49 using 20% sodium hydroxide solution.

C3-9.9 gms of Polyacrylate-33 was added to 90.1 gms of C1 and mixed until uniform with slight heating to 50-60° C. pH was adjusted to 6.41 using 20% sodium hydroxide solution.

Example 2

Mildness Testing via Trans Epithelium Permeation (TEP) Test

Inventive examples E1-E5 and comparative examples C1-C3 were tested for TEP as per the method detailed set forth above, TEP scores shown in Table 3A and Table 3B.

TABLE 3A

| Sample | TEP: $EC_{50}$ |
| --- | --- |
| E1 | 37.06 +/− 2.41 |
| E2 | 4.83 +/− 0.17 |
| E3 | 35.70 +/− 8.13 |
| E4 | 3.68 +/− 0.21 |
| E5 | 3.78 +/− 0.36 |

TABLE 3B

| Sample | *TEP: $EC_{50}$ |
| --- | --- |
| C1 | 0.92 +/− 1.27 |
| C2 | 0.94 +/− 0.96 |
| C3 | 1.16 +/− 1.01 |

*Average of 2 replicates

As shown in tables 3A and 3B, inventive examples E1-E5 demonstrated superior mildness in TEP assay whereas comparative examples C1-C3 showed potential for membrane-damage that may result in penetration of agents via mucosal tissues.

Example 4

Activity of Embodiment E1 Against HIV-1

Following the protocol described above, embodiment E1 was tested against HIV-1 (Table 4).

TABLE 4

| Virus | Strain | Tropism/Subtype | E1 EC50 (µg/ml) |
| --- | --- | --- | --- |
| HIV-1 | IIIB | CXCR4/B | 6.0 |

As shown in Table 4, inventive example E1 exhibits activity at concentrations from about 6 ug/mL against HIV-1.

What is claimed is:

1. A method of inhibiting entry of enveloped viruses into cells comprising contacting said viruses with an anti-viral composition comprising at least one hydrophobically modified polymer having a number average molecular weight ($M_n$) of more than 100,000 as measured by gel permeation chromatography (GPC) calibrated with a poly(methyl methacrylate) (PMMA) standard,
   wherein the hydrophobically modified polymer is a hydrophobically modified alkali swellable emulsion polymer, which is polyacrylate-33,
   wherein the amount of said hydrophobically modified polymer is from about 0.00005% to about 3% by weight of the anti-viral composition,
   wherein the anti-viral composition comprises less than about 9% by weight of surfactant having an HLB greater than about 12,
   wherein said contacting is done by applying the anti-viral composition to skin or mucosal tissue of a subject,
   wherein the formulated anti-viral composition, upon application that contacts the enveloped viruses, inhibits entry of the enveloped viruses into cells, and
   wherein the enveloped virus is human immunodeficiency virus type 1 (HIV-1).

2. The method of claim 1, wherein the anti-viral composition comprises from about 0.375% to less than about 9% by weight of surfactant.

3. The method of claim 2, wherein the anti-viral composition comprises between about 0.375% and 6% by weight of surfactant.

4. The method of claim 2, wherein the anti-viral composition comprises between about 0.375% and 3% by weight of surfactant.

5. The method of claim 1, wherein the trans-epithelial permeability (TEP) of the anti-viral composition is greater than about 3.7.

6. The method of claim 1, wherein the mucosal tissue comprises tissue selected from the group consisting of oral tissue, ocular tissue, nasal tissue, vaginal tissue, rectal tissue and a combination thereof.

7. The method of claim 1, wherein the anti-viral composition further comprises at least 55% of water.

8. The method of claim 7, wherein the anti-viral composition comprises at least 97% of water.

9. The method of claim 1, wherein the inhibition of virus entry into said cells results in the reduction of potential for viral infection.

10. The method of claim 1, wherein the anti-viral composition does not substantially disrupt biological surfaces.

11. The method of claim 1, wherein the anti-viral composition comprises a dosage form selected from the group consisting of: a liquid, a lotion, a cream, a gel, a stick, a spray, a shaving cream, an ointment, a cleansing liquid wash, a solid bar, a shampoo, a paste, a powder, a mousse, a wipe, a patch, a wound dressing, an adhesive bandage, a hydrogel and a film.

12. The method of claim 1, wherein the anti-viral composition further comprises nonoxynol-9.

* * * * *